United States Patent
Vergez et al.

(10) Patent No.: US 6,521,255 B2
(45) Date of Patent: Feb. 18, 2003

(54) OSMOTIC DEVICE CONTAINING RANITIDINE AND A PROKINETIC AGENT

(75) Inventors: Juan A. Vergez, Buenos Aires (AR); Joaquina Faour, Buenos Aires (AR)

(73) Assignee: Osmotica Corp., Tortola (VG)

( * ) Notice: Subject to any disclaimer, the term of this patent is extended or adjusted under 35 U.S.C. 154(b) by 0 days.

(21) Appl. No.: 09/755,294

(22) Filed: Jan. 5, 2001

(65) Prior Publication Data

US 2001/0051185 A1 Dec. 13, 2001

Related U.S. Application Data

(60) Provisional application No. 60/175,844, filed on Jan. 13, 2000.

(51) Int. Cl.[7] ............................................. A61K 9/22

(52) U.S. Cl. ..................... 424/473; 424/468; 424/480; 424/482

(58) Field of Search .................. 424/473, 468, 424/472, 476, 479, 480, 482, 474, 477, 478, 481

(56) References Cited

U.S. PATENT DOCUMENTS 6,004,582 A    12/1999    Faour et al.
6,132,771 A   *   10/2000    Depui et al. ................ 424/468

OTHER PUBLICATIONS

Lederer, P.C. et al., Abstract: Drugs Modifiying Motility in Ulcer Therapy, Z Gastroenterol, Aug. 25, 1987 Suppl. 3: 175–180.

Tytgat, G.N. et al., Abstract: The Medical Therapy of Reflux Oesophagitis, Bailieres Clin Gastroenterol, Oct. 1, 1987 (4): 791–807.

Testoni, P.A. et al., Abstract: Effectiveness of cisapride in gastric ulcer. Results of a double–blind randomized trial versus ranitidine and versus cisapride plus ranitidine, J Clin Gastroenterol, Jul.; 1993 17(1): 5–9.

Inauen, W. et al., Abstract: Effects of ranitidine and cisapride on acid reflux and oesophageal motility in patient with reflux oesophagitis: a 24 hour ambulatory combined pH and manometry study., Gut, Aug.; 1993 34 (8): 1025–1031.

Stubberod, A. et al., Abstract: The effect of cisapride and ranitidine as monotherapies and in combination in the treatment of uncomplicated gastric ulceration, Scand J Gastroenterol, Feb.; 1995 30 (2): 106–110.

McKenna, C.J. et al., Abstract: Combination of ranitidine and cisapride in the treatment of reflux oesophagitis., Eur J Gastrenterol Hepatol, Sep.; 1995 7 (9): 817–822.

Vigneri, S. et al., Abstract: A comparison of five maintenance therapies for reflux esophagitis, N Eng J Med, Oct. 26, 1995 333 (17): 1106–1110.

(List continued on next page.)

Primary Examiner—James M. Spear
(74) Attorney, Agent, or Firm—Rick Matos; Innovar, L.L.C.

(57) ABSTRACT

The present invention provides an osmotic device containing controlled release ranitidine in the core in combination with a prokinetic agent in a rapid release external coat. A wide range of prokinetic agents can be used in this device. Particular embodiments of the invention provide osmotic devices having predetermined release profiles. One embodiment of the osmotic device includes an external coat that has been spray coated rather compression coated onto the device. The device with spray-coated external core is smaller and easier to swallow than the similar device having a compression-coated external coat. The device is useful for the treatment of gastric acid related disorders. The device can be tailored for once or twice daily administration. The amounts of ranitidine and prokinetic agent can be varied. One embodiment provides two different charges of ranitidine (one rapid release and the other controlled release) and a rapid release charge of prokinetic agent.

32 Claims, 2 Drawing Sheets

OTHER PUBLICATIONS

Hill, S.L. et al., Abstract: Proarrhythmia associated with cisapride in children, Pediatrics, Jun.; 1998 101 (6): 1053–1056.

Ryberg, B. et al., Abstract: Omeprazole and ranitidine, antisecretagogues with different modes of action, are equally effective in causing hyperplasia of enterochromaffin–like cells in rat stomach, Regul Pept, May; 1989 25 (2): 235–246.

De Bree, H. et al., Abstract: Kinetics of rate controlled rectally administered ranitidine to male volunteers, Pharm Weekbl [Sci], Jun. 19, 1987; 9 (3): 179–182.

Dal Negro, R. et al., Abstract: Combined administration of controlled release theophylline and ranitidine: a 53–day controlled survey in patients with chronic obstructive lung disease (Cold) and peptic disease., Br J Clin Pract, Nov.; 1987 41 (11): 1004–1008.

* cited by examiner

OSMOTIC DEVICE CONTAINING RANITIDINE AND A PROKINETIC AGENT

CROSS-REFERENCE TO EARLIER FILED APPLICATION

The present application claims the priority of U.S. provisional application for patent Ser. No. 60/175,844 filed Jan. 13, 2000.

FIELD OF THE INVENTION

This invention pertains to an osmotic device containing ranitidine. More particularly, it pertains to an osmotic device tablet which provides a controlled release of ranitidine and a prokinetic agent, following a particularly advantageous release profile.

BACKGROUND OF THE INVENTION

Gastroesophageal reflux disease (GERD), reflux oesophagitis, peptic ulcer, gastric ulcer and other gastric acid related disorders are disorders having a pathogenesis related to reduced gastric motility, i.e., reduced clearing capacity of the stomach, and release of excessive gastric acid. Aside from behavioral changes, GERD and gastric ulcer have been successfully treated with a range of gastric acid inhibitors, such as ranitidine and omeprazole, which are known as H2 blocker or acid-suppressing drugs. Stimulation of gastric motility has been proposed to accelerate the healing of gastric ulcer. Prokinetic drugs, such as cisapride, are known to enhance gastrointestinal motility and prevent duodeno-gastric reflux, and are widely used to treat GERD. Ranitidine and prokinetic drugs have been used in combination to treat gastric ulcer and other related disorders.

Ranitidine is commercially available in tablet, liquid and capsule dosage forms from Geneva Farms, Glaxo Wellcome (Zantac™), Boehringer Ingelheim, Mylan, Novopharm N.C., Ranbaxy, Torpharm, Wockhardt and Zenith Goldline. The tablets and capsules are available in 150 and 300 mg strengths.

Osmotic devices and other tablet formulations are known for their ability to provide a controlled release of a wide range of drugs. Such osmotic devices and other tablet formulations are disclosed in U.S. Pat. No. 4,014,334 to Theeuwes et al., U.S. Pat. No. 4,576,604 to Guittard et al., Argentina Patent No. 234,493, U.S. Pat. No. 4,673,405 to Guittard et al., U.S. Pat. No. 5,558,879 to Chen et al., U.S. Pat. No. 4,810,502 to Ayer et al., U.S. Pat. No. 4,801,461 to Hamel et al., U.S. Pat. No. 5,681,584 to Savastano et al., U.S. Pat. No. 3,845,770, U.S. Pat. No. 6,004,582to Faour et al., and Argentina Patent No. 199,301, the entire disclosures of which are hereby incorporated by reference.

These references, however, do not disclose osmotic devices that provide the specific plasma profiles or release profiles for ranitidine (RNT) that the present invention provides. Moreover, the prior art does not disclose an osmotic device containing a combination of ranitidine with a prokinetic agent, wherein the ranitidine and prokinetic agent are provided according to specific release profiles.

SUMMARY OF THE INVENTION

The osmotic devices of the present invention seek to overcome the disadvantages found in known ranitidine formulations. These osmotic devices provide improved therapeutic benefits over conventional devices.

In one aspect, the present invention provides an osmotic device comprising:

a core comprising a therapeutically effective amount of ranitidine and at least one osmotic agent or osmopolymer; and a semipermeable membrane surrounding the core and having a passageway there through;

wherein the core provides a controlled release of RNT, and at least 60% of the RNT is released within 20 hours after exposure of the osmotic device to an aqueous solution.

Another aspect of the present invention provides an osmotic device for delivering ranitidine and a prokinetic agent comprising:

a core comprising a therapeutically effective amount of ranitidine and at least one osmotic agent or osmopolymer;

a semipermeable membrane surrounding the core and having a passageway there through; and an external coat comprising a therapeutically effective amount of a prokinetic agent and ranitidine;

wherein the core provides a controlled release of RNT, and at least 60% of the RNT is released from the core within 20 hours after exposure of the osmotic device to an aqueous solution, and the external coat provides a rapid release of the prokinetic agent, and at least 75% of the prokinetic agent is released within 1 hour and 80% of RNT in the external coat is released within 1 hour after exposure of the osmotic device to an aqueous solution.

In still other preferred embodiments, the external coat is applied by spray-coating or compression-coating. By spray coating rather than compression coating the external coat, a thinner external coat, and therefore a smaller osmotic device, is formed.

Another aspect of the invention provides a method of treating a gastric acid related disorder in a mammal. This method comprises the step of administering an osmotic device, which provides a controlled release of RNT from its core and a rapid release of a prokinetic agent and RNT from an external coat and RNT, wherein at least 75% of the prokinetic agent is released within about 40 minutes, and at least about 75% of the RNT in the external coat is released within about 1 hour after administration. Gastric acid-related disorders include, for example, gastric ulcer, peptic ulcer, GERD (gastroesophageal reflux disease), and reflux esophagitis.

Figure 1:
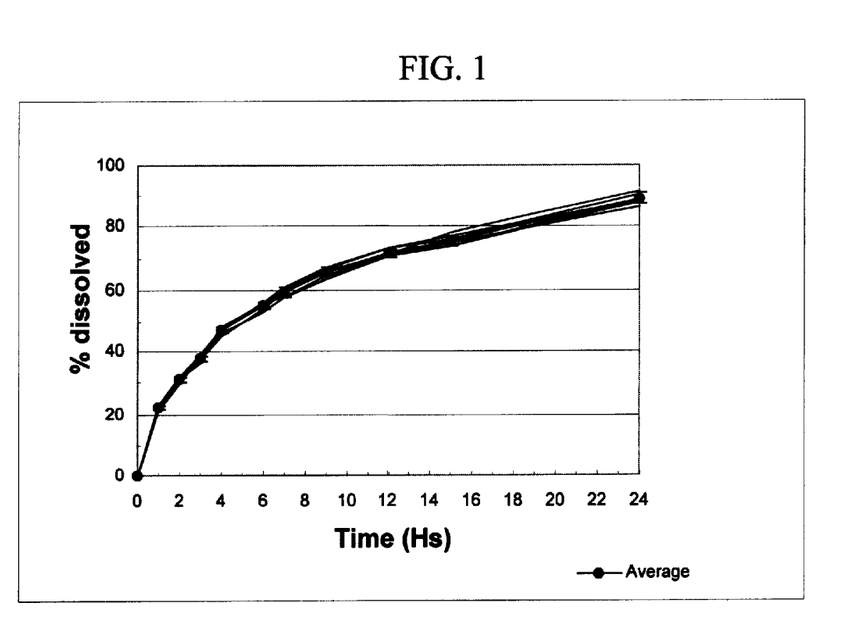
FIG. 1 depicts an in vitro dissolution profile for RNT from the exemplary formulation of Example 1.
Figure 2:
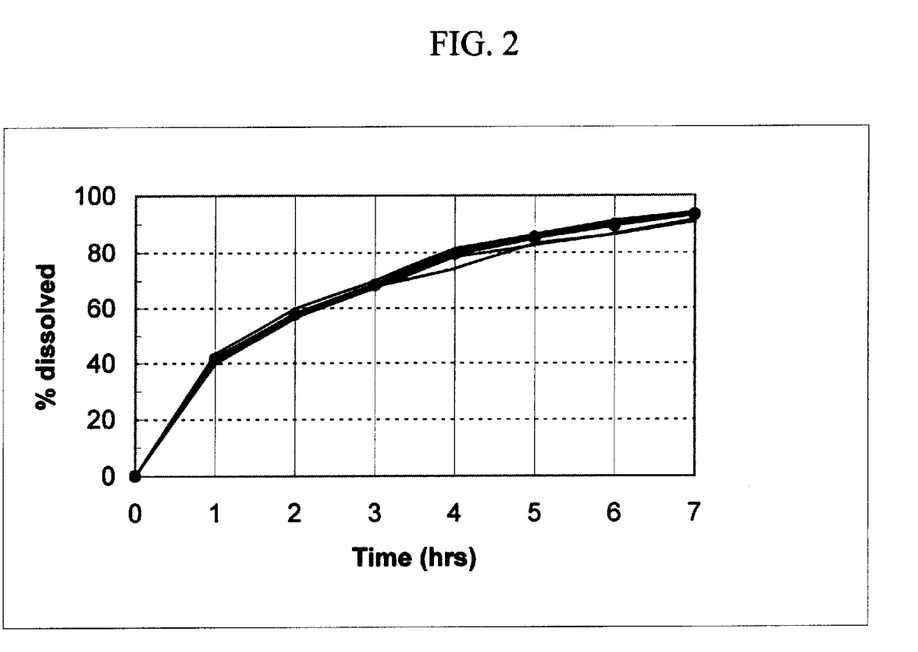
FIG. 2 depicts an in vitro dissolution profile for RNT from a second exemplary formulation.
Figure 3:
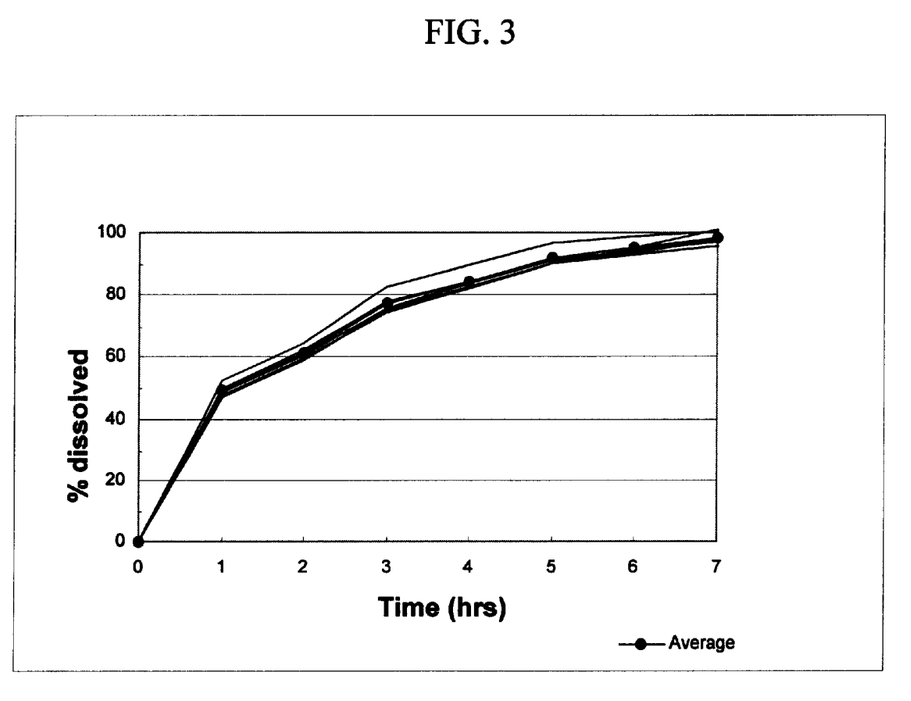
FIG. 3 depicts an in vitro dissolution profile for RNT from a third exemplary formulation.

In other preferred embodiments, the osmotic device provides: a) an RNT release profile similar to that shown in any of FIGS. 1–3; or b) an osmotic device made according to example 1. In still other preferred embodiments, the release of RNT and/or the prokinetic agent has a delayed onset.

In still other preferred embodiments, the prokinetic agent is selected from the group consisting of cisapride, mosapride, domperidone and clevopride.

The osmotic device generally delivers the prokinetic agent to the upper GI tract and the ranitidine to the middle to lower GI tract.

The device can be tailored for once or twice daily administration. The amounts of ranitidine and prokinetic agent can be varied. One embodiment provides two different charges of ranitidine (one rapid release and the other controlled release) and a rapid release charge of prokinetic agent. This embodiment rapidly provides the therapeutic benefit of both drugs so that gastric discomfort is relieved shortly after administration.

Other features, advantages and embodiments of the invention will become apparent to those skilled in the art by the following description, accompanying examples.

BRIEF DESCRIPTION OF THE DRAWINGS

The following drawings are part of the present specification and are included to further demonstrate certain aspects of the invention. The invention may be better understood by reference to one or more of these drawings in combination with the detailed description of the specific embodiments presented herein.

DETAILED DESCRIPTION OF THE INVENTION

Ranitidine and prokinetic agents are available from large number of commercial sources such as Aldrich Chemical Co. or Sigma Chemical Co. or pharmaceutical manufacturers. The invention provides for the administration of ranitidine alone or in combination with a prokinetic agent, wherein these compounds are in their free base, free acid, racemic, optically pure, diastereomeric and/or pharmaceutically acceptable salt forms.

As used herein, "pharmaceutically acceptable salts" refer to derivatives of the disclosed compounds wherein the therapeutic compound is modified by making acid or base salts thereof. Examples of pharmaceutically acceptable salts include, but are not limited to, mineral or organic acid salts of the RNT or prokinetic agent. The pharmaceutically acceptable salts include the conventional non-toxic salts, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartic, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Lists of suitable salts are found in *Remington's Pharmaceutical Sciences*, 17th ed., Mack Publishing Company, Easton, Pa., 1985, p. 1418, the disclosure of which is hereby incorporated be reference.

The phase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

FIG. 1 depicts various ranitidine in vitro release profiles for the osmotic device tablets described in Example 1. This formulation exhibits a 24-hour or greater controlled release of RNT. The RNT release profile of this exemplary 300 mg strength tablet formulation is generally described as follows:

| Time (h) | Maximum Released (%) | Minimum Released (%) |
|---|---|---|
| 1 | 30 | 15 |
| 2 | 37 | 25 |
| 3 | 44 | 32 |
| 4 | 53 | 40 |
| 6 | 61 | 48 |

-continued

| Time (h) | Maximum Released (%) | Minimum Released (%) |
|---|---|---|
| 7 | 66 | 53 |
| 9 | 72 | 59 |
| 12 | 78 | 66 |
| 15 | 83 | 69 |
| 24 | 100 | 82 |

FIG. 2. depicts various RNT in vitro release profiles for 150 mg strength osmotic device tablets made according to a formulation similar to, but than, the formulation of Example 1. This exemplary device provides a controlled release of RNT for a period of about 7 hours after administration. The in vitro release profile can be generally characterized as follows:

| Time (h) | Maximum Released (%) | Minimum Released (%) |
|---|---|---|
| 1 | 49 | 35 |
| 2 | 65 | 52 |
| 3 | 75 | 62 |
| 4 | 87 | 69 |
| 5 | 92 | 78 |
| 6 | 96 | 82 |
| 7 | 100 | 86 |

FIG. 3. depicts various RNT in vitro release profiles for 75 mg strength osmotic device tablets made according to a formulation similar to, but than, the formulation of Example 1. This exemplary device provides a controlled release of RNT for a period of about 7 hours after administration. The in vitro release profile can be generally characterized as follows:

| Time (h) | Maximum Released (%) | Minimum Released (%) |
|---|---|---|
| 1 | 57 | 42 |
| 2 | 70 | 54 |
| 3 | 88 | 70 |
| 4 | 95 | 77 |
| 5 | 99 | 85 |
| 6 | 100 | 88 |
| 7 | 100 | 90 |

Depending upon the particular combination of ingredients used to prepare the osmotic device, it will generally provide an expected overall ranitidine release profile resembling a pseudo-first order, first-order, pseudo-second order, second order, pseudo-third order, or third order release profile.

All of the tablet formulations of the invention will provide therapeutically effective levels of ranitidine and a prokinetic agent for at least a predetermined period of time. The tablets of the invention will generally provide therapeutically effective amounts of ranitidine for a period of not less than 18 hours and not more than 30 hours, preferably not less than 20 hours and not more than 28 hours, and more preferably not less than 22 hours and not more than 24 hours. According to another preferred embodiment, the tablets provide a controlled release of RNT for a period of about 5–10 hours and, preferably about 7 hours.

Specific embodiments of the method of the invention for treating gastric acid related disorders include those wherein: 1) the osmotic device releases ranitidine for a period of up to about 12 hours and is administered twice daily; 2) the osmotic device provides a therapeutic plasma level in the mammal for a period of up to about 12 hours; 3) the osmotic device releases ranitidine for a period of at least 18 hours and is administered once daily; 4) the osmotic device provides a therapeutic plasma level in the mammal for a period of up to about 24 hours; 5) the osmotic device delivers the prokinetic agent to the upper GI tract and the ranitidine to at least the upper and middle gastrointestinal tract of the mammal to which the device is administered orally; 6) the release of the RNT, the prokinetic agent or both has a delayed onset; 7) the prokinetic agent is selected from the group consisting of cisapride, mosapride, domperidone and clevopride; and/or 8) the gastric acid-related disorder is selected from the group consisting of gastric ulcer, peptic ulcer, gastroesophageal reflux disease, and reflux esophagitis.

The osmotic device of the invention provides an improved therapeutic benefit over conventional devices containing only ranitidine or a prokinetic agent. By providing the ranitidine and prokinetic agent according to the dissolution or release criteria described herein, an enhanced therapeutic result is obtained.

The external coating can be an immediately dissolving coating that dissolves in the buccal cavity or a rapidly dissolving coating that dissolved in the stomach, jejunum or duodenum. The controlled release core generally begins to release ranitidine within about 2 hours after administration.

The rapid release coating will release all of its prokinetic agent, within three hours after administration, and preferably at least 75% of its prokinetic agent within about 40 minutes after administration.

Those of ordinary skill in the art will appreciate that the particular amounts of ranitidine and prokinetic agent used in the osmotic device will vary according to, among other things, the desired pharmacokinetic behavior in a mammal.

When a rapidly dissolving coat is used in the tablet formulations of the invention, the coat will generally comprise an inert and non-toxic material that is at least partially, and preferably substantially completely, soluble or erodible in an environment of use. The rapidly dissolving coat will be soluble in the buccal cavity and/or upper GI tract, such as the stomach, duodenum, jejunum or upper small intestines. Exemplary materials are disclosed in U.S. Pat. Nos. 4,576, 604 and 4,673,405, and the text Pharmaceutical Dosage Forms: Tablets Volume 1, Second Edition. A. Lieberman. ed. 1989, Marcel Dekker, Inc. the relevant disclosures of which are hereby incorporated by reference. In preferred embodiments, the rapidly dissolving coat will be soluble in saliva, gastric juices, or acidic fluids.

The long acting controlled release tablet formulations that provide a delayed and sustained release of ranitidine may include an enteric coat which is soluble or erodible in intestinal juices, substantially pH neutral or basic fluids but for the most part insoluble in gastric juices or acidic fluids. A wide variety of other polymeric materials are known to possess these various solubility properties. Such other polymeric materials include, by way of example and without limitation, cellulose acetate phthalate (CAP), cellulose acetate trimelletate (CAT), poly(vinyl acetate) phthalate (PVAP), hydroxypropyl methylcellulose phthalate (HP), poly(methacrylate ethylacrylate) (1:1) copolymer (MA-EA), poly(methacrylate methylnethacrylate) (1:1) copolymer (MA-MMA), poly(methacrylate methylmethacrylate) (1:2) copolymer, Eudragit L-30-D™ (MA-EA, 1:1), Eudragit™ L-100-55T (MA-EA, 1:1), hydroxypropyl methylcellulose acetate succinate (HPMCAS), Coateric™ (PVAP), Aquater- icTm (CAP), AQUACOAT™ (HPMCAS) and combinations thereof. The enteric coat can also comprise dissolution aids, stability modifiers, and bioabsorption enhancers.

When the enteric coat is intended to be dissolved, eroded or become detached from the core in the colon, materials such as hydroxypropylcellulose, microcrystalline cellulose (MCC, Avicel™ from FMC Corp.), poly (ethylene-vinyl acetate) (60:40) copolymer (EVAC from Aldrich Chemical Co.), 2-hydroxyethyhnethacrylate (HEMA), MMA, terpolymers of HEMA: MMA:MA synthesized in the presence of N,N'-bis(methacryloyloxyethyloxycarbonylamino)-azobenzene, azopolymers, enteric coated timed release system (Time Clock® from Pharmaceutical Profiles, Ltd., UK) and calcium pectinate can be used.

A preferred polymeric material for use in the enteric coat involves enteric materials that resist the action of gastric fluid avoiding permeation through the semipermeable wall while one or more of the materials in the core of the tablet are solubilized in the intestinal tract thereby allowing delivery of the ranitidine in the core by osmotic pumping in an osmotic device to begin. A material that easily adapts to this kind of requirement is a poly(vinylpyrrolidone)-vinyl acetate copolymer, such as the material supplied by BASF under its Kollidon VA64 trademark, mixed with magnesium stearate and other similar excipients. The enteric coat can also comprise povidone, which is supplied by BASF under its Kollidon K 30 trademark, and hydroxypropyl methylcellulose, which is supplied by Dow under its Methocel E-15 trademark. The materials can be prepared in solutions of having different concentrations of polymer according to the desired solution viscosity. For example, a 10% P/V aqueous solution of Kollidon K 30 has a viscosity of about 5.5–8.5 cps at 20° C., and a 2% P/V aqueous solution of Methocel E-15 has a viscosity of about 13–18 cps at 20° C.

The enteric coat can comprise one or more materials that do not dissolve, disintegrate, or change their structural integrity in the stomach and during the period of time that the tablet resides in the stomach. Representative materials that keep their integrity in the stomach can comprise a member selected from the group consisting of (a) keratin, keratin sandarac-tolu, salol (phenyl salicylate), salol beta-naphthylbenzoate and acetotannin, salol with balsam of Peru, salol with tolu, salol with gum mastic, salol and stearic acid, and salol and shellac; (b) a member selected from the group consisting of formalized protein, formalized gelatin, and formalized cross-linked gelatin and exchange resins; (c) a member selected from the group consisting of myristic acid-hydrogenated castor oil-cholesterol, stearic acid-mutton tallow, stearic acid-balsam of tolu, and stearic acid-castor oil; (d) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (e) a member selected from the group consisting of abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethylmethacrylate-butylmethacrylate-methylmethacrylate copolymer of 150,000 molecular weight, methacrylic acid-methylmethacrylate 50:50 copolymer of 135,000 molecular weight, methacrylic acid-methylmethacrylate-30:70-copolymer of 135,000 mol.

wt., methacrylic acid-dimethylaminoethyl-methacrylate-ethylacrylate of 750,000 mol. wt., methacrylic acid-methylmethacrylate-ethylacrylate of 1,000,000 mol. wt., and ethylacrylate-methylmethacrylate-ethylacrylate of 550,000 mol. wt; and, (g) an enteric composition comprising a member selected from the group consisting of cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and other materials known to one or ordinary skill in the art.

The semipermeable membrane of the osmotic device is formed of a material that is substantially permeable to the passage of fluid from the environment of use to the core and substantially impermeable to the passage of active agent from the core. Many common materials known by those of ordinary skill in the art are suitable for this purpose. Exemplary materials are cellulose esters, cellulose ethers and cellulose esters-ethers. However, it has been found that a semipermeable membrane consisting essentially of cellulose acetate (CA) and poly(ethylene glycol) (PEG), in particular PEG 400, are preferred when used in combination with the other materials required in the present osmotic device. This particular combination of CA and PEG provides a semipermeable membrane that gives the osmotic device a well controlled release profile for the active agent in the core and that retains its chemical and physical integrity in the environment of use. The ratio of CA:PEG generally ranges from about 50–99% by weight of CA: about 50–1% by weight of PEG, and preferably about 95% by weight of CA: about 5% by weight of PEG. The ratio can be varied to alter permeability and ultimately the release profile of the osmotic device. Other preferred materials can include a selected member of the group of cellulose acylates such as cellulose acetate, cellulose diacetate, cellulose triacetate and combinations thereof. Many suitable polymers, include those disclosed in Argentine Patent No. 199,301 and other references cited herein, the disclosures of which are hereby incorporated by reference.

The core of all the osmotic device tablet of the present invention will comprise ranitidine, at least one pharmaceutically acceptable excipient and optionally one or more other materials. Generally, the tablet formulations will comprise about 0.1–99.9% by weight of ranitidine in the uncoated tablet core. Preferred ranges will vary according to prokinetic agent used and the intended use of the osmotic device.

When the controlled release tablet is an osmotic device, osmotically effective solutes, osmotic agents or osmagents are added. These osmagents can aid in either the suspension or dissolution of the RNT in the core. Exemplary osmagents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art. Osmagents can also be incorporated to the core of the osmotic device to control the release of RNT therefrom.

The tablets of the invention can also comprise an acidifying agent, alkalizing agent, adsorbent, antioxidant, buffering agent, colorant, flavorant, sweetening agent, tablet antiadherent, tablet binder, tablet and capsule diluent, tablet direct compression excipient, tablet disintegrant, tablet glidant, tablet lubricant, tablet or capsule opaquant and/or tablet polishing agents.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and other materials known to one of ordinary skill in the art.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

As used herein, the term "acidifying agent" is intended to mean a compound used to provide an acidic medium for product stability. Such compounds include, by way of example and without limitation, acetic acid, amino acid, citric acid, fumaric acid and other alpha hydroxy acids, such as hydrochloric acid, ascorbic acid, and nitric acid and others known to those of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and other materials known to one of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and other materials known to one of ordinary skill in the art.

As used herein, the term "tablet antiadherents" is intended to mean agents which prevent the sticking of tablet formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "tablet binders" is intended to mean substances used to cause adhesion of powder particles in table granulations. Such compounds include, by way of example and without limitation, acacia, alginic acid, carboxymethylcellulose sodium, poly(vinylpyrrolidone), compressible sugar (e.g., NuTab), ethylcellulose, gelatin, liquid glucose, methylcellulose, povidone and pregelatinized starch and other materials known to one of ordinary skill in the art.

When needed, binders may also be included in the tablets. Exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC F68, PLURONIC F127), collagen, albumin, gelatin, cellulosics in nonaqueous solvents, combinations thereof and the like. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "tablet and capsule diluent" or "fillers" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "tablet direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "tablet glidant" is intended to mean agents used in tablet and capsule formulations to reduce friction during tablet compression. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "tablet/capsule opaquant" is intended to mean a compound used to render a capsule or a tablet coating opaque. May be used alone or in combination with a colorant. Such compounds include, by way of example and without limitation, titanium dioxide and other materials known to one of ordinary skill in the art.

As used herein, the term "tablet polishing agent" is intended to mean a compound used to impart an attractive sheen to coated tablets. Such compounds include, by way of example and without limitation, carnauba wax, and white wax and other materials known to one of ordinary skill in the art.

As used herein, the term "tablet disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose(e.g., Avicel), carboxymethylcellulose calcium, cellulose polyacrilin potassium (e.g., Amberlite), alginates, sodium starch glycolate, gums such as agar, guar, locust bean, karaya, pectin, tragacanth and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors that have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly preferred flavors are the grape and cherry flavors and citrus flavors such as orange.

The present tablets can also employ one or more commonly known surface active agents or cosolvents that improve wetting or disintegration of the tablet core or layers.

Plasticizers can also be included in the tablets to modify the properties and characteristics of the polymers used in the coats or core of the tablets. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly (propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in *Poly(ethylene glycol) Chemistry: Biotechnical and Biomedical Applications* (J. M. Harris, Ed.; Plenum Press, NY) the disclosure of which is hereby incorporated by reference.

The tablets of the invention can also include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly (oxyethylene)-block-poly(oxypropylene) copolymers; and amphoteric detergents, for example, alkyl P-aminopropionates and 2-alkylimidazoline quaternary ammonium salts; and mixtures thereof Various other components, not otherwise listed above, can be added to the present formulation for optimization of a desired active agent release profile including, by way of example and without limitation, glycerylmonostearate, nylon, cellulose acetate butyrate, d, 1-poly(lactic acid), 1,6-hexanediamine, diethylenetriamine, starches, derivatized starches, acetylated monoglycerides, gelatin coacervates, poly (styrene - maleic acid) copolymer, glycowax, castor wax, stearyl alcohol, glycerol palmitostearate, poly(ethylene), poly(vinyl acetate), poly (vinyl chloride), 1,3-butylene-glycoldimethacrylate, ethyleneglycol-dimethacrylate and methacrylate hydrogels.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

By the term "effective amount", it is understood that, with respect to, for example, pharmaceuticals, a therapeutically effective amount is contemplated. A therapeutically effective amount is the amount or quantity of ranitidine which is sufficient to elicit the required or desired therapeutic response, or in other words, the amount which is sufficient to elicit an appreciable biological response when administered to a patient.

The tablets of the invention can assume any shape or form known in the art of pharmaceutical sciences. The device of the invention can be a pill, sphere, tablet, bar, plate, paraboloid of revolution, ellipsoid of revolution or the like. The tablets can also include surface markings, cuttings, grooves, letters and/or numerals for the purposes of decoration, identification and/or other purposes.

The tablets of the invention can be prepared according to the methods disclosed herein or those well known in the art, more specifically according to the methods disclosed in the disclosure incorporated herein by reference. For example, according to one manufacturing technique, ranitidine and excipients that comprise the core are mixed in solid, semi-solid or gelatinous form, then moistened and sieved through a specified screen to obtain uncoated cores. The uncoated cores are then dried in a dryer and compressed, for example, by punching. The compressed and uncoated cores are then covered with a semipermeable membrane. Subsequently, the semipermeable membrane surrounding the core should be perforated with, for example, laser equipment. Finally, an external coat containing the prokinetic agent is applied to the semipermeable membrane.

The external coat can be applied as a compression-coating, but it is preferably applied as a spray-on coating. The sprayed-on coating is thinner and lighter than the compression coating, and an osmotic device including the sprayed on external coating is, therefore, smaller than a similar osmotic device having a compression coat. A smaller size osmotic device generally results in increased patient compliance in taking the osmotic device and is therefore advantageous.

The tablets of the invention can be coated with a finish coat as is commonly done in the art to provide the desired shine, color, taste or other aesthetic characteristics. Materials suitable for preparing the finish coat are well known in the art and found in the disclosures of many of the references cited and incorporated by reference herein.

The advantages of the present system over known systems for administering ranitidine in combination with a prokinetic agent is improved therapeutic benefit, simplified manufacturing, and increased patient compliance.

The following examples should not be considered exhaustive, but merely illustrative of only a few of the many embodiments contemplated by the present invention. The methods described herein can be followed to prepare osmotic devices according to the invention.

EXAMPLE 1

A large scale batch of ranitidine HCl (350±35 mg strength) and cisapride monohydrate (10±5 mg) strength tablets was prepared by mixing 292.95 g of ranitidine HCl, 68.05 g of microcrystalline cellulose, 50.00 g of povidone, 3.50 g of colloidal silicon dioxide. The mixture was blended to homogenize; then, 4.50 g of magnesium stearate was added as lubricant. This blend was tabletted to 800 mg–1000 mg/core and hardness of 8–12 kp with flat faced, 13.0-mm diameter punches. The slugs were milled by passing through a standard USP 20-mesh screen and were blended with 3.50 g of colloidal silicon dioxide and 4.50 g of magnesium stearate. The final blend was tabletted using biconcaves, 10 mm diameter punches. Cores weight: 407 mg Hardness from 15 to 20 kp.

A first composition (for the semipermeable membrane) to cover the cores was prepared as follows: 47.79 g of cellulose acetate and 2.52 g of polyethylene glycol 400 in a mixture of methylene chloride-methyl alcohol 70:30 v/v (volume/volume). This polymer mixture was sprayed onto the cores in a conventional pan coater to obtain film-coated tablets whose membrane coating weighed 50.4 mg approximately. A 0.50-mm hole was drilled through the coating in one face of the tablet.

A second composition (for the inert water soluble coating) to cover the film-coated tablets was prepared as follows: 3.90 g of copolyvidone, 3.50 g of titanium dioxide, 0.10 g of Aluminum Lake Brilliant Blue and 12.50 g of talc were mixed in isopropyl alcohol. This polymer mixture was sprayed onto the tablets in a conventional pan coater to obtain film-coated tablets whose membrane coating weighed 20 mg approximately.

A third coating (for the water soluble drug-containing coating) was prepared by mixing 55.80 g of ranitidine HCl, 10.39 g of cisapride monohydrate, 200.00 g of microcrystalline cellulose and 1.50 g of colloidal silicon dioxide. The mixture was blended to homogenize; then, 4.00 g of magnesium stearate was added as lubricant. This blend was tabletted to 800–1000 mg/core and hardness of 8–12 kp with 13.0-mm diameter flat faced punches. The slugs were milled by passing through a standard USP 20-mesh screen and were blended with 211.31 g of microcrystalline cellulose, 10.0 g of crospovidone, 1.5 g of colloidal silicon dioxide and 5.5 g of magnesium stearate. This final blend was tabletted using 14-mm diameter biconcaves punches, surrounding the previous film-coated tablets which layer coating weighed 500.3 mg. Hardness: 14–18 kp.

A fourth composition (for the inert water soluble coating) to cover the previous tablets was prepared as follows: 18.18 g of hydroxypropyl methylcellulose 2910, 5.18 g of polyethylene glycol 6000 and 6.64 g of titanium dioxide were mixed in a mixture of methylene chloride-alcohol 96°. This polymer mixture was sprayed onto the tablets in a conventional pan coater to obtain film-coated tablets which membrane weighed 30 mg approximately.

Tablets made according to the above describe procedure generally had a formulation as follows:

Ranitidine HCl 300 mg+Cisapride monohydrate 10 mg

| CORE | |
| --- | --- |
| Ranitidine Hydrochloride | 292.950 mg |
| Microcrystalline Cellulose | 68.050 mg |
| Colloidal Silicon Dioxide | 7.000 mg |
| Povidone | 30.000 mg |
| Magnesium Stearate | 9.000 mg |
| COATING A | |
| Cellulose Acetate | 47.790 mg |
| Polyethylene Glycol 400 | 2.520 mg |
| COATING B | |
| Copolyvidone | 3.900 mg |
| Titanium Dioxide | 3.500 mg |
| Talc | 12.500 mg |
| Aluminum Lake Brilliant Blue | 0.100 mg |
| COATING C | |
| Ranitidine Hydrochloride | 55.800 mg |
| Cisapride Monohydrate | 10.390 mg |
| Microcrystalline Cellulose | 411.310 mg |
| Crospovidone | 10.000 mg |
| Colloidal Silicon Dioxide | 3.000 mg |
| Magnesium Stearate | 9.500 mg |

| -continued | |
| --- | --- |
| COATING D | |
| Hydroxypropyl methylcellulose 2910 | 18.180 mg |
| Polyethylene Glycol 6000 | 5.180 mg |
| Titanium Dioxide | 6.640 mg |

EXAMPLE 2

An osmotic device according to the invention was prepared according to Example 1 except that only 175±20 mg total of ranitidine salt was used and lesser amounts of other ingredients were used. A large scale batch of Ranitidine HCl (175±20 mg strength) and cisapride monohydrate (10±5 mg strength) tablets was prepared by mixing 140.62 g. of ranitidine HCl, 60.83 g of microcrystalline cellulose, 16.95 g of povidone, 2.80 g of colloidal silicon dioxide. The mixture was blended to homogeneity. Then, 3.0 g of magnesium stearate was added as lubricant. This blend was tabletted to 800–1000 mg/core and hardness of 8–12 kp with 13.0-mm diameter flat faced punches. The slugs were milled by passing through a standard USP 20-mesh screen and were blended with 2.8 g of colloidal silicon dioxide and 3.0 g of magnesium stearate. The final blend was tabbleted using 10.0-mm diameter biconcaves punches. Core weight: 230 mg. Hardness: 14–16 kp.

A first composition (for the semipermeable membrane) to cover the cores was prepared as follows: 15.20 g of cellulose acetate and 1.60 g of polyethylene glycol 400 in a mixture of methylene chloride-methyl alcohol 70:30 v/v (volume/volume). This polymer mixture was sprayed onto the cores in a conventional pan coater to obtain film-coated tablets which membrane weighed 16.80 mg approximately. A 0.50 mm-hole was drilled trough the coating on one face of the tablet.

A second composition (for the inert water soluble coating) to cover the film-coated tablet was prepared as follows: 3.12 g of copolyvidone, 2.80 g of titanium dioxide, 0.080 g of Aluminum Lake Red Ponceau and 10.0 g of talc were mixed in isopropyl alcohol. This polymer mixture was sprayed onto the tablets in a conventional pan coater to obtain film-coated tablets which membrane weighed 16.0 mg approximately.

A third coating (for the water soluble drug-containing coating) was prepared by mixing 33.48 g of ranitidine HCl, 10.39 g of cisapride monohydrate and 150.0 g of microcrystalline cellulose. The mixture was blended to homogenize; then, 2.75 g of magnesium stearate was added as lubricant. This blend was tabletted to 800–1000 mg/core and hardness of 8–12 kp with 13.0-mm diameter flat faced punches. The slugs were milled by passing through a standard USP 20-mesh screen and were blended with 2.75 g of magnesium stearate. This final blend was tabletted using 12-mm diameter biconcaves punches, surrounding the previous film-coated tablets whose layer coating weighed 362 mg. Hardness: 10–15 kp.

A fourth composition (for the inert water soluble coating) to cover the previous tablets was prepared as follows: 10.89 g of hydroxypropyl methylcellulose 2910, 3.1 g of polyethylene glycol 6000 and 4.01 g of titanium dioxide were mixed in a mixture of methylene chloride-alcohol 96°. This polymer mixture was sprayed onto the tablets in a conventional pan coater to obtain film-coated tablets whose membrane weighed 18 mg approximately.

Tablets made according to this example generally included the following ingredients in the approximate amounts indicated.

| CORE | |
| --- | --- |
| Ranitidine Hydrochloride. | 140.620 mg. |
| Microcrystalline Cellulose | 60.830 mg. |
| Colloidal Silicon Dioxide | 5.600 mg. |
| Povidone | 16.950 mg. |
| Magnesium Stearate | 6.000 mg. |
| COATING A | |
| Cellulose Acetate | 15.200 mg. |
| Polyethylene Glycol 400 | 1.600 mg. |
| COATING B | |
| Copolyvidone | 3.120 mg. |
| Titanium Dioxide | 2.800 mg. |
| Aluminum Lake Red Ponceau | 0.080 mg. |
| Talc | 10.000 mg. |
| COATING C | |
| Ranitidine Hydrochloride | 33.480 mg. |
| Cisapride Monohydrate | 10.390 mg. |
| Microcrystalline Cellulose | 306.130 mg. |
| Magnesium Stearate | 5.500 mg. |
| Colloidal Silicon Dioxide | 1.500 mg. |
| Cropovidone | 5.000 mg. |
| COATING D | |
| Hydroxypropyl methylcellulose 2910 | 10.890 mg. |
| Polyethylene Glycol 6000 | 3.100 mg. |
| Titanium Dioxide | 4.010 mg. |

This exemplary formulation provided a release profile similar to that of FIG. 2.

EXAMPLE 3

An osmotic device according to the invention was prepared according to Example 1 except that only about 85±10 mg total of ranitidine salt was used and lesser amounts of other ingredients were used. A large scale batch of ranitidine HCl (85±10 mg strength) and cisapride monohydrate (10±5 mg strength) tablets was prepared by mixing 64.45 g of ranitidine HCl, 31.82 g of microcrystalline cellulose, 7.25 g of povidone, 0.19 g of colloidal silicon dioxide. The mixture was blended to homogenize; then, 0.55 g of magnesium stearate was added as lubricant. This blend was tabletted to 800–1000 mg/core and hardness of 8–12 kp with 13.0-mm diameter flat faced punches. The slugs were milled by passing through a standard USP 20-mesh screen and were blended with 0.19 g of colloidal silicon dioxide and 0.55 g of magnesium stearate. The final blend was tabletted using 6.50-mm diameter biconcave punches. Cores weight: 105 mg. Hardness: 10–14 kp.

A first composition (for the semipermeable membrane) to cover the cores was prepared as follows: 12.13 g of cellulose acetate and 1.27 g of polyethylene glycol 400 in a mixture of methylene chloride-methyl alcohol 70:30 v/v (volume/volume). This polymer mixture was sprayed onto the cores in a conventional pan coater to obtain film-coated tablets which membrane weighed approximately 13.40 mg. A 0.50 mm-hole was drilled trough the coating in one face of the tablet.

A second composition (for the inert water soluble coating) to cover the film-coated tablet was prepared as follows: 2.61 g of copolyvidone, 2.35 g of titanium dioxide, 0.070 g of Aluminum Lake Red Ponceau and 8.38 g of talc were mixed in isopropyl alcohol. This polymer mixture was sprayed onto the tablets in a conventional pan coater to obtain film-coated tablets which membrane weighed approximately 13.40 mg.

A third coating (for the water soluble drug-containing coating) was prepared by mixing 22.32 g of ranitidine HCl, 10.39 g of cisapride monohydrate and 100.0 g of microcrystalline cellulose. The mixture was blended to homogeneity; then, 2.0 g of magnesium stearate was added as lubricant. This blend was tabletted to 800–1000 mg/core and hardness of 8–12 kp with, 13.0-mm diameter flat faced punches. The slugs were milled by passing through a standard USP 20-mesh screen and were blended with 1.35 g of colloidal silicon dioxide, 4.21 g of crospovidone and 2.0 g of magnesium stearate. This final blend was tabletted using 12-mm diameter biconcave punches, surrounding the previous film-coated tablets which layer coating weighed 250.0 mg. Hardness: 10–14 kp.

A fourth composition (for the inert water soluble coating) to cover the previous tablets was prepared as follows: 7.26 g of hydroxypropyl methylcellulose 2910, 2.07 g of polyethylene glycol 6000 and 2.67 g of titanium dioxide were mixed in a mixture of methylene chloride-alcohol 96°. This polymer mixture was sprayed onto the tablets in a conventional pan coater to obtain film-coated tablets which membrane weighed 12 mg approximately.

Tablets made according to the above-described procedure generally included the following ingredients in the approximate amounts indicated.

| | Amount |
| --- | --- |
| CORE | |
| Ranitidine Hydrochloride. | 64.450 mg. |
| Microcrystalline Cellulose | 31.820 mg. |
| Colloidal Silicon Dioxide | 0.380 mg. |
| Povidone | 7.250 mg. |
| Magnesium Stearate | 1.100 mg. |
| COATING A | |
| Cellulose Acetate | 12.130 mg. |
| Polyethylene Glycol 400 | 1.270 mg. |
| COATING B | |
| Copolyvidone | 2.610 mg. |
| Titanium Dioxide | 2.350 mg. |
| Aluminum Lake Red Ponceau | 0.070 mg. |
| Talc | 8.380 mg. |
| COATING C | |
| Ranitidine Hydrochloride | 22.320 mg. |
| Cisapride Monohydrate | 10.390 mg. |
| Microcrystalline Cellulose | 207.730 mg. |
| Magnesium Stearate | 4.000 mg. |
| Colloidal Silicon Dioxide | 1.350 mg. |
| Crospovidone | 4.210 mg. |
| COATING D | |
| Hydroxypropylmethylcellulose 2910 | 7.260 mg. |
| Polyethylene Glycol 6000 | 2.070 mg. |
| Titanium Dioxide | 2.670 mg. |

This exemplary formulation provided a release profile similar to that of FIG. 3.

EXAMPLE 4

An osmotic device according to the invention was prepared according to Example 1 and generally containing the following ingredients in the approximate amounts indicated.

|  | Range |
|---|---|
| CORE | |
| Ranitidine salt | 140 ± 15 mg |
| Microcrystalline Cellulose (Filler) | 50.50–70.00 mg |
| Colloidal Silicon Dioxide (Glidant) | 2.50–6.50 mg |
| Povidone (Binder) | 10.50–18.00 mg |
| Magnesium Stearate (Lubricant) | 0.50–6.70 mg |
| Semipermeable coat | |
| Cellulose Acetate (Cellulose ester) | 10.50–19.20 mg |
| Polyethylene Glycol 400 (Plasticizer) | 0.50–4.00 mg |
| Inert water soluble coat (optional) | |
| Copolyvidone (Water soluble polymer) | 1.50–3.50 mg |
| Titanium Dioxide (Opaquant) | 0.50–4.00 mg |
| Aluminum Lake Red Ponceau (Colorant) | 0.01–0.09 mg |
| Talc (Filler) | 1.50–18.0 mg |
| Drug-containing water soluble coat | |
| Ranitidine salt (optional) | 33.5 ± 5 mg |
| Prokinetic agent | 10.4 ± 5 mg |
| Microcrystalline Cellulose (Filler) | 200.00–350.0 mg |
| Magnesium Stearate (Lubricant) | 1.50–7.50 mg |
| Colloidal Silicon Dioxide (Glidant) | 1.00–3.50 mg |
| Crospovidone (Disintegrant) | 4.00–10.50 mg |
| Finish coat (optional) | |
| Hydroxypropyl methylcellulose 2910 (Water soluble polymer) | 8.90–18.50 mg |
| Polyethylene Glycol 6000 (Plasticizer) | 2.50–6.00 mg |
| Titanium Dioxide (Opaquant) | 2.50–7.00 mg |

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

We claim:

1. An osmotic device comprising:
   a core comprising a therapeutically effective amount of ranitidine (RNT) and at least one osmotic agent or osmopolymer, wherein the core provides a controlled release of RNT, and a least 60% of the RNT is released from the core within 20 hours after exposure of the osmotic device to an aqueous solution;
   a semipermeable membrane surrounding the core and having a passageway there through; and
   an external coat comprising a therapeutically effective amount of a prokinetic agent and ranitidine, wherein at least 75% of the prokinetic agent is released within 1 hour and at least 80% of the RNT in the external coat is released within 1 hour after exposure of the osmotic device to an aqueous solution.

2. The osmotic device of claim 1, wherein the external coat is applied by spray coating.

3. The osmotic device of claim 1, wherein the external coat is applied by compression coating.

4. The osmotic device of claim 1, wherein the osmotic device comprises about 200–400 mg of ranitidine salt and the osmotic device provides a dissolution profile approximating the following when exposed to an aqueous environment:

| Time (h) | Maximum Released (%) | Minimum Released (%) |
|---|---|---|
| 1 | 30 | 15 |
| 2 | 37 | 25 |
| 3 | 44 | 32 |
| 4 | 53 | 40 |
| 6 | 61 | 48 |
| 7 | 66 | 53 |
| 9 | 72 | 59 |
| 12 | 78 | 66 |
| 15 | 83 | 69 |
| 24 | 100 | 82 |

5. The osmotic device of claim 1, wherein the osmotic devices comprises about 100–200 mg of ranitidine salt and provides a ranitidine dissolution profile approximating the following when exposed to an aqueous environment:

| Time (h) | Maximum Released (%) | Minimum Released (%) |
|---|---|---|
| 1 | 49 | 35 |
| 2 | 65 | 52 |
| 3 | 75 | 62 |
| 4 | 87 | 69 |
| 5 | 92 | 78 |
| 6 | 96 | 82 |
| 7 | 100 | 86 |

6. The osmotic device of claim 1, wherein the osmotic devices comprises about 50–100 mg of and provides a ranitidine dissolution profile approximating the following when aqueous environment:

| Time (h) | Maximum Released (%) | Minimum Released (%) |
|---|---|---|
| 1 | 57 | 42 |
| 2 | 70 | 54 |
| 3 | 88 | 70 |
| 4 | 95 | 77 |
| 5 | 99 | 85 |
| 6 | 100 | 88 |
| 7 | 100 | 90 |

7. The osmotic device of claim 5 comprising the following ingredients in the approximate amounts indicated:

|  | Range |
|---|---|
| CORE | |
| Ranitidine salt | 140 ± 15 mg |
| Filler | 50.50–70.00 mg |
| Glidant | 2.50–6.50 mg |
| Binder | 10.50–18.00 mg |
| Semipermeable coat | |
| Cellulose ester | 10.50–19.20 mg |
| Plasticizer | 0.50–4.00 mg |
| Inert water soluble coat (optional) | |
| Water soluble polymer | 1.50–3.50 mg |
| Opaquant | 0.50–4.00 mg |
| Filler | 1.50–18.0 mg |

-continued

| | Range |
|---|---|
| Drug-containing water soluble coat | |
| Ranitidine salt (optional) | 33.5 ± 5 mg |
| Prokinetic agent | 10.4 ± 5 mg |
| Filler | 200.00–350.0 mg |
| Disintegrant | 4.00–10.50 mg |
| Finish coat (optional) | |
| Water soluble polymer | 8.90–18.50 mg |
| Plasticizer | 2.50–6.00 mg |
| Opaquant | 2.50–7.00 mg |

8. The osmotic device of claim 7, wherein the inert water soluble coat is present.

9. The osmotic device of claim 8, wherein the finish coat is present.

10. The osmotic device of anyone of claims 1, 4, 5, 6, 7, or 8 wherein the prokinetic agent is selected from the group consisting of cisapride, mosapride, domperidone and clevopride.

11. The osmotic device of claim 10, wherein the osmotic device delivers the prokinetic agent to the upper GI tract and the ranitidine to at least the upper and middle gastrointestinal tract of a mammal to which the device is administered orally.

12. The osmotic device of claim 1, wherein the release of the RNT, the prokinetic agent or both has a delayed onset when the device is administered orally to a mammal.

13. A method of treating a gastric acid related disorder in a mammal comprising the step of orally administering to the mammal an osmotic device that provides a controlled release of ranitidine (RNT) from its core for a period of at least seven hours and a rapid release of a prokinetic agent and ranitidine from an external coat, wherein at least 75% of the prokinetic agent is released within about 40 minutes, and at least about 75% of the RNT in the external coat is released within about 1 hour after administration.

14. The method of claim 13, wherein the osmotic device releases ranitidine for a period of up to about 12 hours and is administered twice daily.

15. The method of claim 14, wherein the osmotic device provides a therapeutic plasma level in the mammal for a period of up to about 12 hours.

16. The method of claim 15, wherein the osmotic device releases ranitidine for a period of at least 18 hours and is administered once daily.

17. The method of claim 16, wherein the osmotic device provides a therapeutic plasma level in the mammal for a period of up to about 24 hours.

18. The method of claim 13, wherein the osmotic device delivers the prokinetic agent to the upper GI tract and the ranitidine to at least the upper and middle gastrointestinal tract of the mammal to which the device is administered orally.

19. The method of claim 13, wherein the release of the RNT, the prokinetic agent or both has a delayed onset.

20. The method of anyone of claims 13–19, wherein the prokinetic agent is selected from the group consisting of cisapride, mosapride, domperidone and clevopride.

21. The method of claim 20, wherein the gastric acid-related disorder is selected from the group consisting of gastric ulcer, peptic ulcer, gastroesophageal reflux disease, and reflux esophagitis.

22. The method of claim 13, wherein the release of the RNT, the prokinetic agent or both has a delayed onset.

23. A method of treating a gastric acid related disorder in a mammal comprising the step of orally administering to the mammal an osmotic device according to any one of claims 1, 4, 5, 6, 7, or 8.

24. A method of treating a gastric acid related disorder in a mammal comprising the step of orally administering to the mammal an osmotic device according to claim 10.

25. A method of treating a gastric acid related disorder in a mammal comprising the step of orally administering to the mammal an osmotic device according to claim 11.

26. A method of treating a gastric acid related disorder in a mammal comprising the step of orally administering to the mammal an osmotic device according to claim 12.

27. A controlled release dosage form comprising a first composition comprising a therapeutically effective amount of ranitidine, a second composition comprising a therapeutically effective amount of a prokinetic agent, wherein the dosage form provides a controlled release of ranitidine and an immediate release of the prokinetic agent, and wherein the dosage form further provides an immediate release of ranitidine.

28. The dosage form of claim 27, wherein ranitidine is provided in immediate release form in the second composition.

29. A controlled release dosage form comprising a therapeutically effective amount of ranitidine and a therapeutically effective amount of a prokinetic agent, wherein the dosage form provides a controlled release of ranitidine and an immediate release of ranitidine and the prokinetic agent.

30. An osmotic device comprising:
   an external coat comprising a first charge of ranitidine and a prokinetic agent;
   a core comprising a second charge of ranitidine; and
   a membrane enveloping the core and surrounded by the external coat, wherein the membrane has at least one aperture or pore therethrough to permit release of ranitidine from the core.

31. An osmotic device comprising:
   a core comprising a therapeutically effective amount of ranitidine;
   a membrane enveloping the core and comprising at least one aperture or pore therethrough to permit release of ranitidine from the core; and
   an external coat comprising a therapeutically effective amount of a prokinetic agent.

32. A method of treating a gastric related disorder in a mammal comprising the step of administering to the mammal a single dosage form that provides a controlled release of ranitidine and an immediate release of a prokinetic agent, wherein the dosage form further provides an immediate release of ranitidine.

* * * * *